(12) United States Patent
Livengood

(10) Patent No.: US 11,779,782 B1
(45) Date of Patent: Oct. 10, 2023

(54) NOSTRIL-SHIELDING NASAL MASK AND ASSOCIATED METHOD(S)

(71) Applicant: Blake Livengood, St. Johns, FL (US)

(72) Inventor: Blake Livengood, St. Johns, FL (US)

( * ) Notice: Subject to any disclaimer, the term of this patent is extended or adjusted under 35 U.S.C. 154(b) by 0 days.

(21) Appl. No.: 17/936,250

(22) Filed: Sep. 28, 2022

(51) Int. Cl.
*A61M 16/06* (2006.01)
*A62B 23/06* (2006.01)

(52) U.S. Cl.
CPC ......... *A62B 23/06* (2013.01); *A61M 16/0683* (2013.01); *A61M 2210/0618* (2013.01)

(58) Field of Classification Search
CPC ................ A41D 13/11; A41D 13/1138; A41D 13/1146; A41D 13/1161; A41D 13/1184; A41D 2300/32; A45D 44/12; A61B 5/085; A61B 5/091; A61F 5/08; A61M 15/0013; A61M 15/0018; A61M 15/0021; A61M 16/0488; A61M 16/049; A61M 16/0493; A61M 16/06; A61M 16/0683; A61M 16/10; A61M 16/1045; A61M 16/16; A61M 16/201; A61M 16/208; A61M 16/209; A61M 2205/3334; A61M 2205/3344; A61M 5/1723; A62B 18/006; A62B 18/02; A62B 18/025; A62B 18/08; A62B 18/084; A62B 23/02; A62B 23/025; A62B 23/06; A62B 25/00; A62B 7/10; A62B 9/003; A63B 23/18; B65D 43/162; B65D 85/70; Y10S 128/909; Y10S 55/13; Y10S 55/35
See application file for complete search history.

(56) References Cited

U.S. PATENT DOCUMENTS

| | | | | |
|---|---|---|---|---|
| 406,118 A | * | 7/1889 | Welch | A61M 16/06 128/204.11 |
| 1,914,418 A | * | 6/1933 | Goyena | A61F 5/08 55/DIG. 35 |
| 2003/0029454 A1 | * | 2/2003 | Gelinas | A62B 18/025 128/205.27 |
| 2017/0065838 A1 | * | 3/2017 | Bunge | A62B 18/084 |
| 2022/0241623 A1 | * | 8/2022 | Ellison | A62B 23/025 |

FOREIGN PATENT DOCUMENTS

WO    WO-2021167533 A1 * 8/2021 ......... A41D 13/1138

* cited by examiner

*Primary Examiner* — Annette Dixon
(74) *Attorney, Agent, or Firm* — Ashkan Najafi

(57) ABSTRACT

A nostril-shielding nasal mask includes an adjustable body including a top portion having a concave shape and is provided with an arcuate anterior face and arcuate posterior face opposed therefrom, a hinge attached to the top portion, and a bottom portion attached to the hinge wherein the bottom portion has a planar shape and is provided with a curvilinear anterior face and a rectilinear posterior face. Such a bottom portion further has a plurality of apertures configured to align with the nostrils of the user, respectively. The nasal mask further includes a scented air filter removably inserted into the bottom portion, and fasteners fixedly attached to the top portion and the bottom portion. Such fasteners ae configured to maintain the top portion and the bottom portion directly abutted against the nose bridge of the user and the nostrils of the user, respectively.

14 Claims, 4 Drawing Sheets

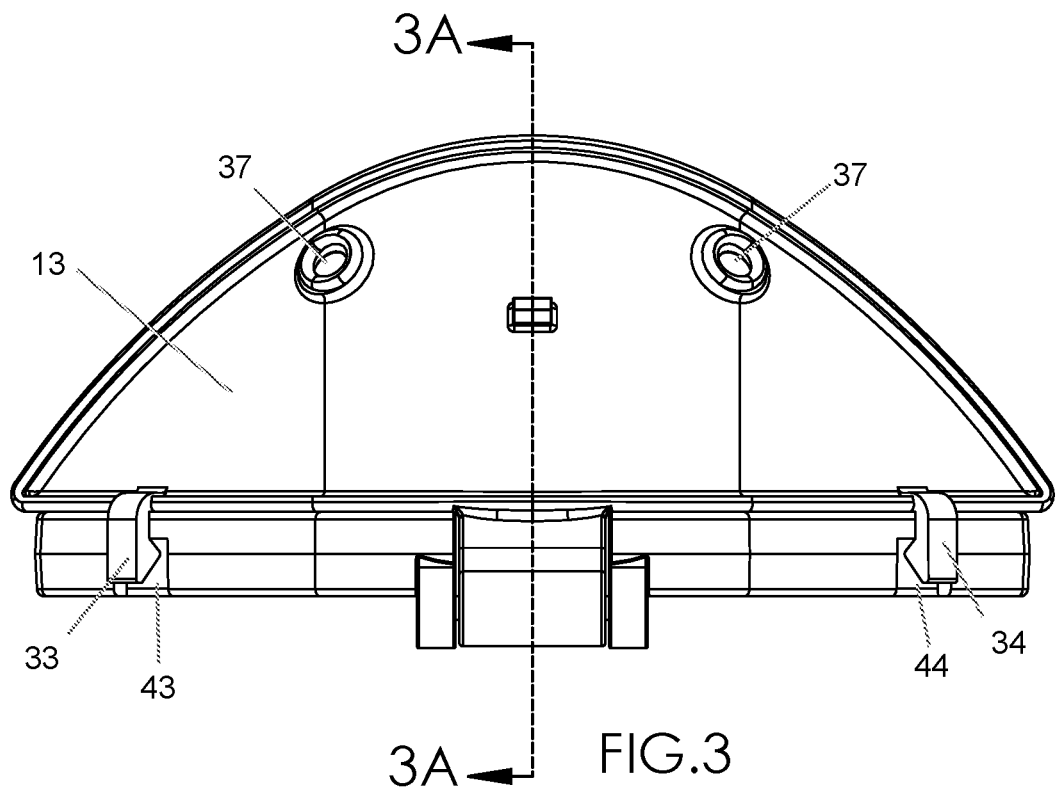
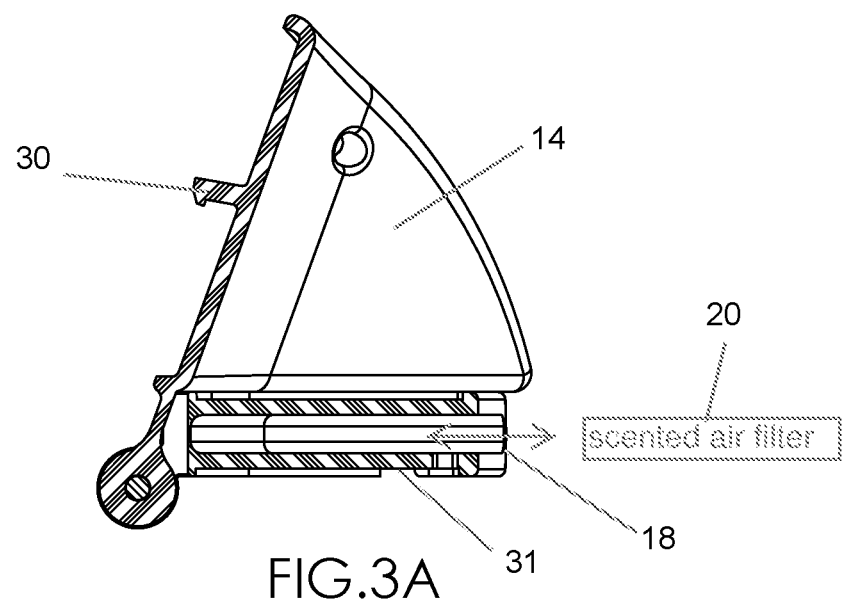

NOSTRIL-SHIELDING NASAL MASK AND ASSOCIATED METHOD(S)

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND

Technical Field

Exemplary embodiment(s) of the present disclosure relate to nasal masks and, more particularly, to a specially configured nostril-shielding nasal mask for filtering ambient air prior to entering a user's nasal passageway.

Prior Art

The nasal cavity is an important organ of human respiration and olfaction, is an important channel for exchanging air between the body and the outside of the body, is also a first place for filtering air and preventing diseases, and is the basis for ensuring the health of the body by keeping the air clean, so that the mask can play the roles of dust prevention and pollution prevention only by absolutely filtering the air entering the nasal cavity. In addition, the nasal cavity is the only olfactory organ of human body, and the olfactory cells in the nasal cavity can generate anaphylactic reaction to foreign matters and dust entering the nasal cavity, including a plurality of spray medicines for treating rhinitis, when the nasal cavity is cleaned or the nasal cavity is sprayed with medicine, anaphylactic reaction can be generated, and sneezing and snivel clearing are usually shown. So that the sprayed medicine is flushed out of the nose by the nasal discharge and cannot achieve the purpose of treatment.

Accordingly, a need remains for a nostril-shielding nasal mask in order to overcome at least one aforementioned shortcoming. The exemplary embodiment(s) satisfy such a need by providing a specially configured nostril-shielding nasal mask that is convenient and easy to use, lightweight yet durable in design, versatile in its applications, and configured for filtering ambient air prior to entering a user's nasal passageway.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a specially configured nostril-shielding nasal mask for filtering ambient air prior to entering a user's nasal passageway. These and other objects, features, and advantages of the non-limiting exemplary embodiment(s) are provided by a nostril-shielding nasal mask including an adjustable body configured to cover a nose bridge and nostrils of a user wherein the adjustable body includes a top portion having a concave shape and is provided with an arcuate anterior face and arcuate posterior face opposed therefrom, a hinge attached to the top portion, and a bottom portion attached to the hinge wherein the bottom portion has a planar shape and is provided with a curvilinear anterior face and a rectilinear posterior face. Such a bottom portion further has a plurality of apertures configured to align with the nostrils of the user, respectively. The bottom portion is indirectly attached to the top portion. The nasal mask further includes a scented air filter removably inserted through the rectilinear posterior face and into the bottom portion wherein the scented air filter is spaced from the top portion, and a plurality of fasteners fixedly attached to the top portion and the bottom portion. Such fasteners ae configured to maintain the top portion and the bottom portion directly abutted against the nose bridge of the user and the nostrils of the user, respectively.

In a non-limiting exemplary embodiment, each of the top portion and the bottom portion is configured to selectively articulated along a common arcuate path defined about a fulcrum axis of the hinge.

In a non-limiting exemplary embodiment, the bottom portion is configured to remain statically abutted directly against the nostrils of the user while the top portion is articulated along the common arcuate path between a first raised, operating position and a first lowered, non-operating position.

In a non-limiting exemplary embodiment, the top portion is configured to remain statically abutted directly against the nose bridge of the user while the bottom portion is articulated along the common arcuate path between a second raised, non-operating position and a second lowered, operating position.

In a non-limiting exemplary embodiment, the arcuate anterior face and the arcuate posterior face are solid and continuously extend between a top edge and a bottom edge of the top portion.

In a non-limiting exemplary embodiment, the plurality of fasteners include a first finger statically attached to the arcuate anterior face and protruding outwardly away therefrom, and a notch disposed at the bottom portion and being configured to receive the first finger when the top portion is articulated to the first lowered, non-operating position. Advantageously, the first finger is frictionally and detachably engaged with the scented air filter when the first finger is interlocked in the notch. Advantageously, such first finger is configured to maintain the scented air filter at the bottom portion when the top portion is articulated downwardly to the first lowered, non-operating position and while the bottom portion is articulated upwardly to the second raised, non-operating position.

In a non-limiting exemplary embodiment, the plurality of fasteners further include a second finger and a third finger spaced therefrom. Each of the second finger and the third finger are affixed to the top portion. A second notch and a third notch are disposed at the curvilinear anterior face of the bottom portion. Advantageously, the second finger and the third finger are directly interlocked with the second notch and the third notch, respectively, when the top portion is disposed at the first raised, operating position and the bottom portion is disposed at the second lowered, operating position.

In a non-limiting exemplary embodiment, the apertures are equidistantly offset from a centrally registered latitudinal axis and configured to align beneath a respective one of the nostrils of the user, respectively.

In a non-limiting exemplary embodiment, the top portion includes a plurality of holes. The plurality of fasteners further include a tether passed through the holes and configured to secure to a head of the user so that the top portion remains directly abutted against the nose bridge of the user while the bottom portion remains abutted directly against the nostrils of the user.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

FIG. 3 is a top plan view of the nostril-shielding nasal mask at the closed position;

FIG. 3A is a cross-sectional view taken along line 3A-3A in FIG. 4;

Figure 1:
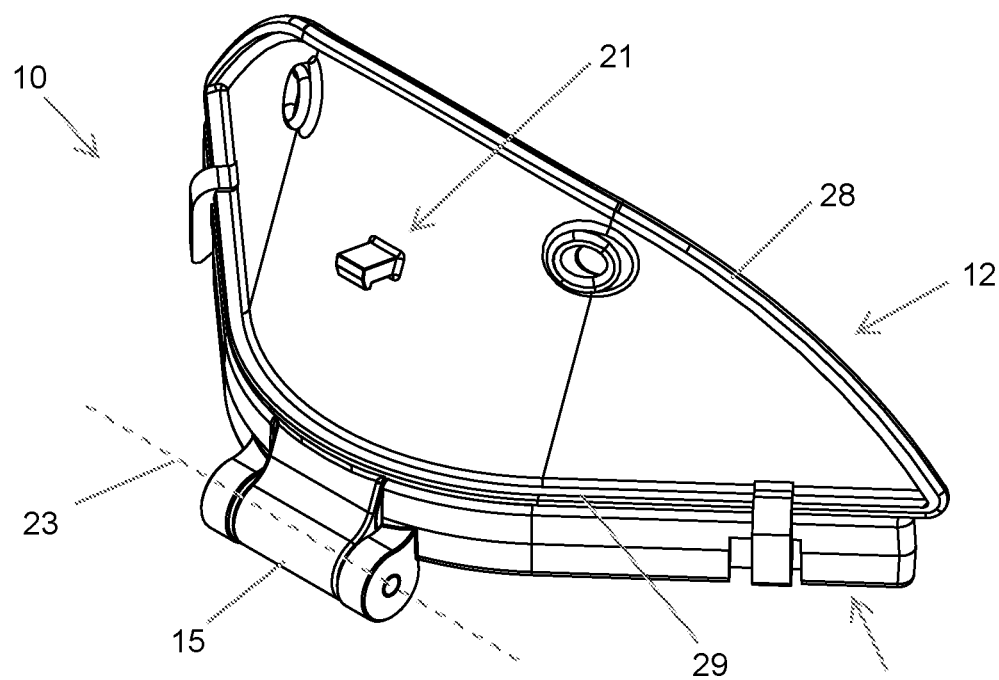
FIG. 1 is a perspective view of a nostril-shielding nasal mask at a closed position, in accordance with a non-limiting exemplary embodiment of the present disclosure; position.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

If used herein, "about," "generally," and "approximately" mean nearly and in the context of a numerical value or range set forth means ±15% of the numerical.

If used herein, "substantially" means largely if not wholly that which is specified but so close that the difference is insignificant.

Figure 2:
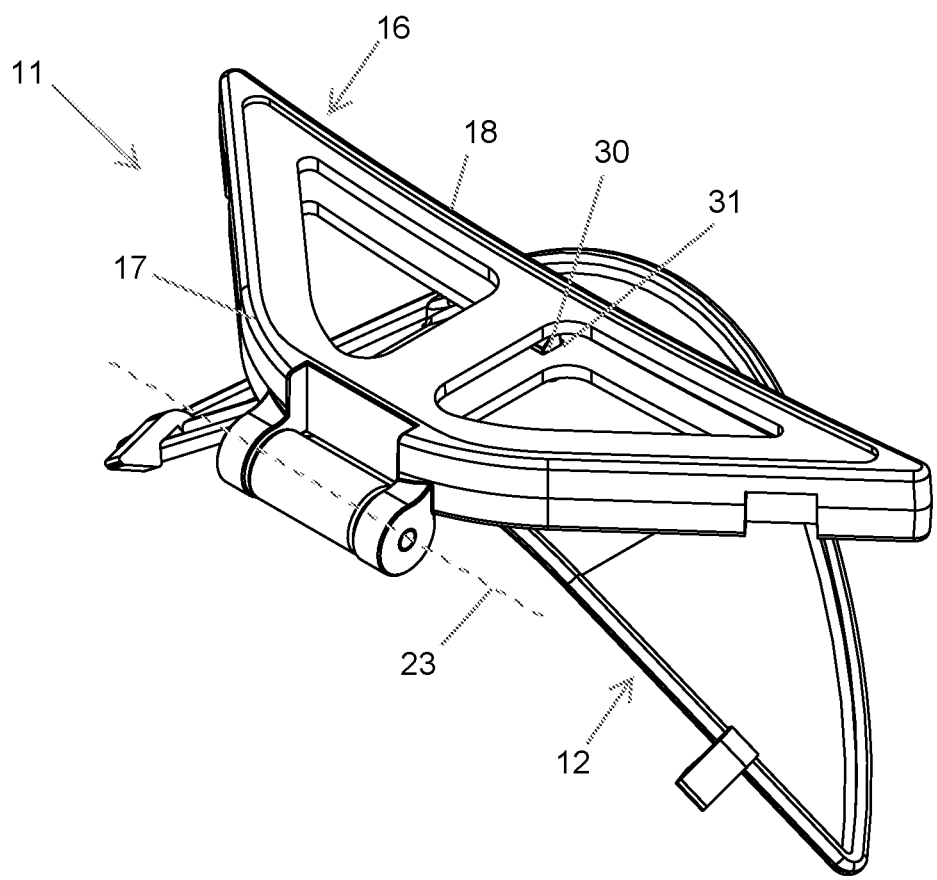
FIG. 2 is a perspective view of the nostril-shielding nasal mask at an open position.
Figure 4:
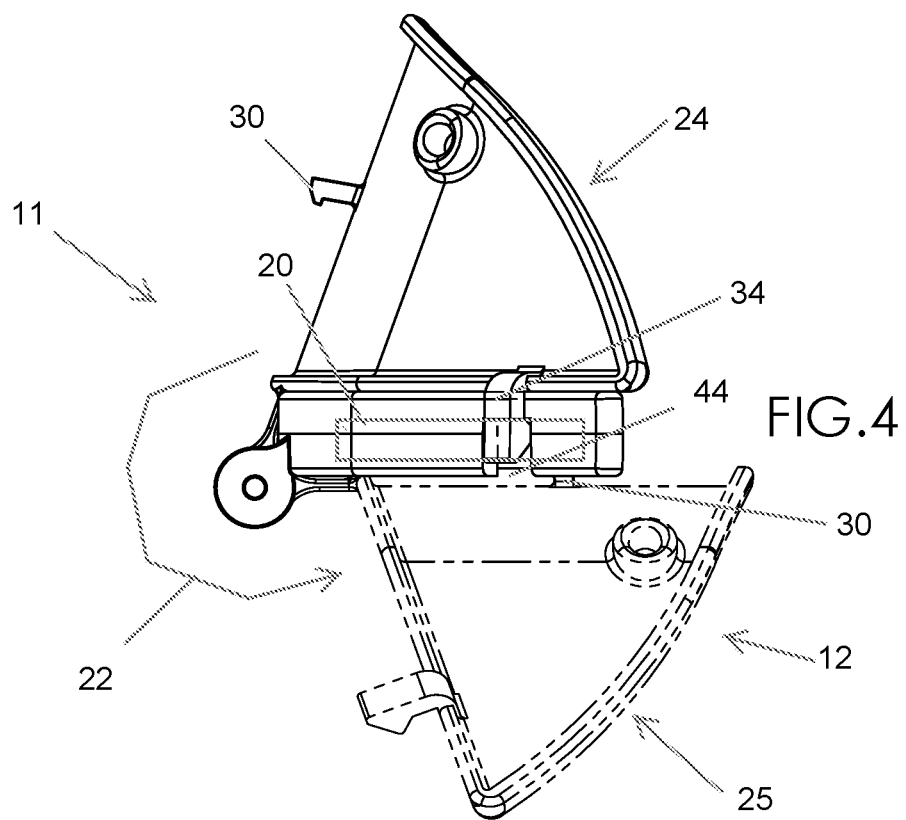
FIG. 4 is a side elevational view showing an top portion of the nasal mask articulated to from a closed position to an open position relative to a stationary position of an air-filter receiving portion.
Figure 5:
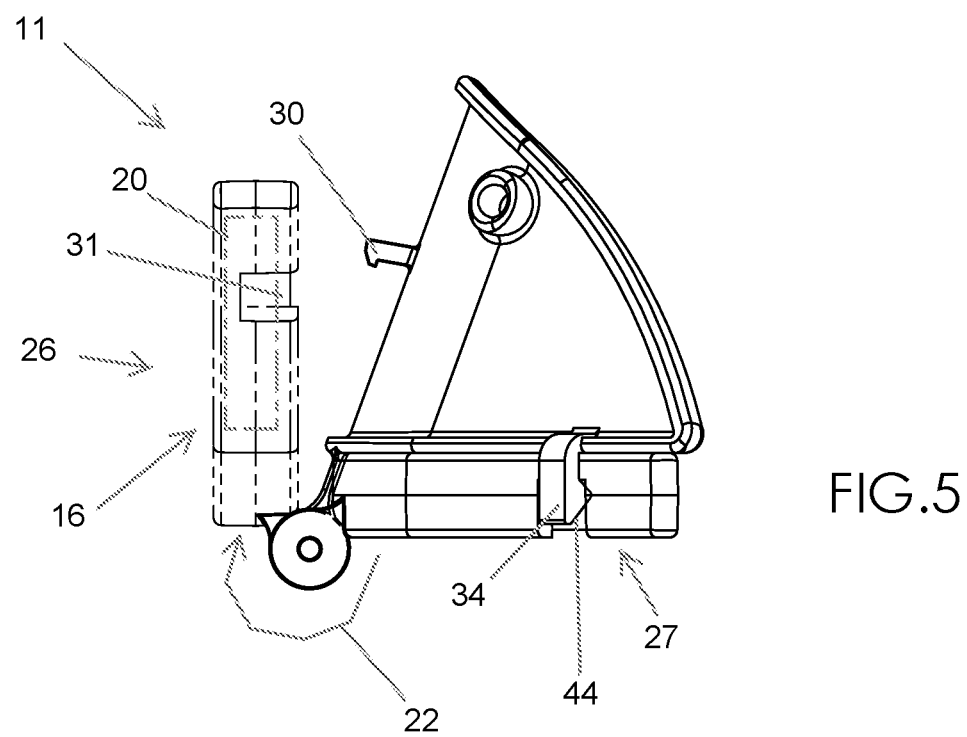
FIG. 5 is a side elevational view showing the top portion of the nasal mask articulated back from the closed position to the open position relative to a stationary position of an air-filter receiving portion.
Figure 6:
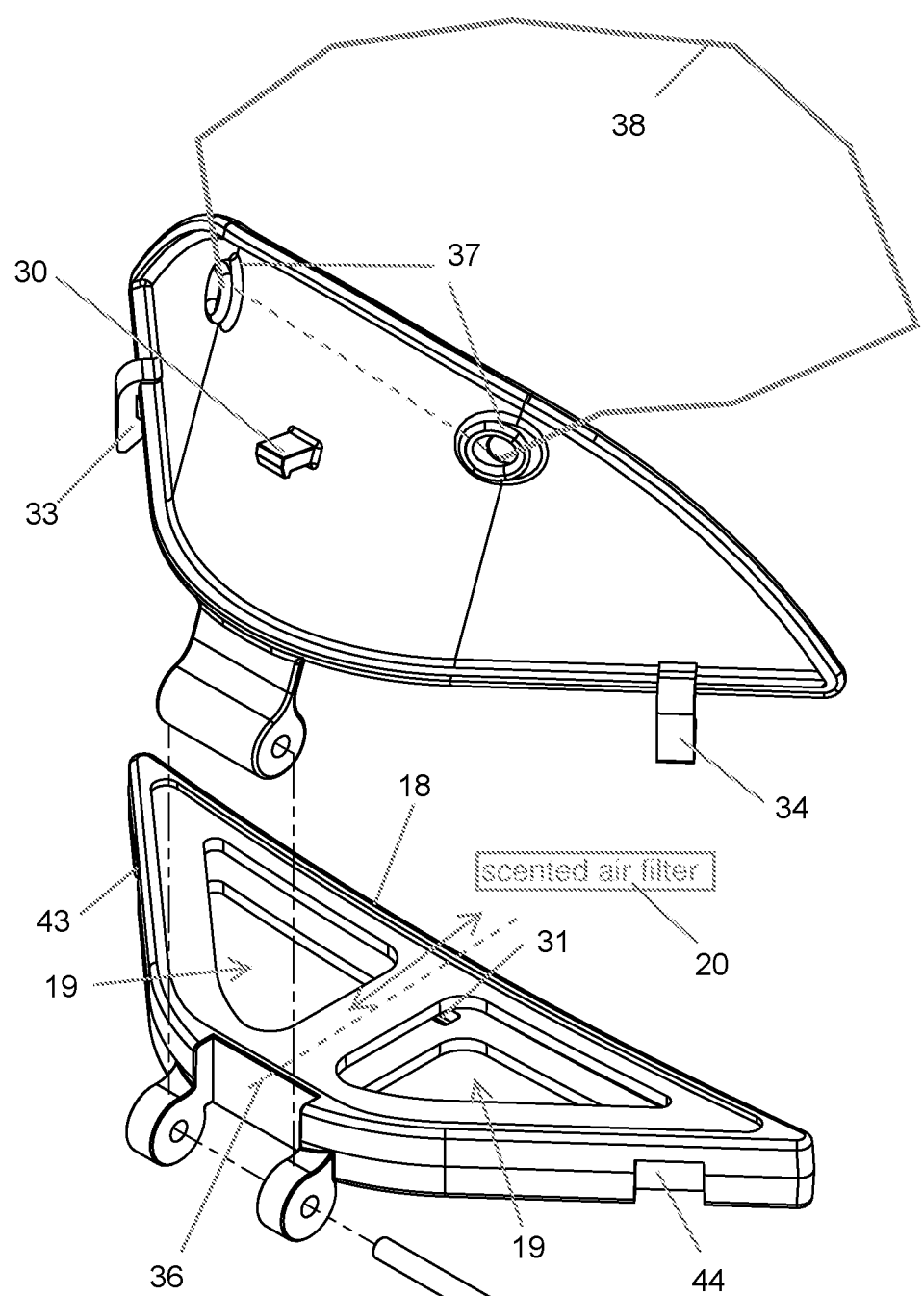
FIG. 6 is an exploded view of the nasal mask.

The non-limiting exemplary embodiment(s) is/are referred to generally in FIGS. 1-6 and is/are intended to provide a specially configured nostril-shielding nasal mask 10 for filtering ambient air prior to entering a user's nasal passageway, and thereby alleviating undesirable smells encountered by a user. The nasal mask 10 may be worn around a user's head or supported on a user's bridge of the nose. The nasal mask 10 is a scented nose-piece, resting on the nose and shielding the user's nostrils to mask odors via natural fruit oils, floral extracts, or other natural scents. The nasal mask 10 may be used in a variety of environments: adult use while changing a child's stinking diaper; janitorial purposes; sewer and water-treatment personnel; factory workers, such as those in poultry, cattle, or pork processing plants; nursing home and hospital applications; and, in any other environment where people encounter unpleasant odors.

Referring to FIGS. 1-6 in general, the nostril-shielding nasal mask 10 includes an adjustable body 11 configured to cover a nose bridge and nostrils of a user wherein the adjustable body 11 includes a top portion 12 having a concave shape and is provided with an arcuate anterior face 13 and arcuate posterior face 14 opposed therefrom, a hinge 15 attached to the top portion 12, and a bottom portion 16 attached to the hinge 15 wherein the bottom portion 16 has a planar shape and is provided with a curvilinear anterior face 17 and a rectilinear posterior face 18. Such a bottom portion 16 further has a plurality of apertures 19 configured to align with the nostrils of the user, respectively. The bottom portion 16 is indirectly attached (via hinge 15) to the top portion 12. The nasal mask 10 further includes a scented air filter 20 removably inserted through the rectilinear posterior face 18 and into the bottom portion 16 wherein the scented air filter 20 is spaced from the top portion 12, and a plurality of fasteners 21 fixedly attached to the top portion 12 and the bottom portion 16. Such fasteners 21 are configured to maintain the top portion 12 and the bottom portion 16 directly abutted against the nose bridge of the user and the nostrils of the user, respectively. Such a structural configuration yields the new, useful, and unpredicted result of ensuring the scented air filter 20 is aligned with the user nostrils, and allows the mask 10 to remain engaged with the user face while the bottom portion 16 is articulated upwardly and downwardly.

In a non-limiting exemplary embodiment, each of the top portion 12 and the bottom portion 16 is configured to selectively articulated along a common arcuate path 22 defined about a fulcrum axis 23 of the hinge 15. Such a structural configuration yields the new, useful, and unpredicted result of ensuring the scented air filter 20 is aligned with the user nostrils, and allows the mask 10 to remain engaged with the user face while the bottom portion 16 is articulated upwardly and downwardly.

In a non-limiting exemplary embodiment, the bottom portion 16 is configured to remain statically abutted directly against the nostrils of the user while the top portion 12 is articulated along the common arcuate path 22 between a first raised, operating position 24 and a first lowered, non-operating position 25. Such a structural configuration yields the new, useful, and unpredicted result of ensuring the scented air filter 20 is aligned with the user nostrils, and allows the mask 10 to remain engaged with the user face while the bottom portion 16 is articulated upwardly and downwardly.

In a non-limiting exemplary embodiment, the top portion 12 is configured to remain statically abutted directly against the nose bridge of the user while the bottom portion 16 is articulated along the common arcuate path 22 between a second raised, non-operating position 26 and a second lowered, operating position 27. Such a structural configuration yields the new, useful, and unpredicted result of ensuring the scented air filter 20 is aligned with the user nostrils, and allows the mask 10 to remain engaged with the user face while the bottom portion 16 is articulated upwardly and downwardly.

In a non-limiting exemplary embodiment, the arcuate anterior face 13 and the arcuate posterior face 14 are solid and continuously extend between a top edge 28 and a bottom edge 29 of the top portion 12. Such a structural configuration yields the new, useful, and unpredicted result of ensuring the scented air filter 20 is aligned with the user nostrils, and allows the mask 10 to remain engaged with the user face while the bottom portion 16 is articulated upwardly and downwardly.

In a non-limiting exemplary embodiment, the plurality of fasteners 21 include a first finger 30 statically attached to the arcuate anterior face 13 and protruding outwardly away therefrom, and a notch 31 disposed at the bottom portion 16 and being configured to receive the first finger 30 when the top portion 12 is articulated to the first lowered, non-operating position 25. Advantageously, the first finger 30 is frictionally and detachably engaged with the scented air filter 20 when the first finger 30 is interlocked in the notch 31. Advantageously, such first finger 30 is configured to maintain the scented air filter 20 at the bottom portion 16 when the top portion 12 is articulated downwardly to the first lowered, non-operating position 25 and while the bottom portion 16 is articulated upwardly to the second raised, non-operating position 26. Such a structural configuration yields the new, useful, and unpredicted result of ensuring the scented air filter 20 is aligned with the user nostrils, and allows the mask 10 to remain engaged with the user face while the bottom portion 16 is articulated upwardly and downwardly.

In a non-limiting exemplary embodiment, the plurality of fasteners 21 further include a second finger 33 and a third finger 34 spaced therefrom. Each of the second finger 33 and the third finger 34 are affixed to the top portion 12. A second notch 43 and a third notch 44 are disposed at the curvilinear anterior face 17 of the bottom portion 16. Advantageously, the second finger 33 and the third finger 34 are directly interlocked with the second notch 43 and the third notch 44, respectively, when the top portion 12 is disposed at the first raised, operating position 24 and the bottom portion 16 is disposed at the second lowered, operating position 27. Such a structural configuration yields the new, useful, and unpredicted result of ensuring the scented air filter 20 is aligned with the user nostrils, and allows the mask 10 to remain engaged with the user face while the bottom portion 16 is articulated upwardly and downwardly.

In a non-limiting exemplary embodiment, the apertures 19 are equidistantly offset from a centrally registered latitudinal axis 36 and configured to align beneath a respective one of the nostrils of the user, respectively. Such a structural configuration yields the new, useful, and unpredicted result of ensuring the scented air filter 20 is aligned with the user nostrils, and allows the mask 10 to remain engaged with the user face while the bottom portion 16 is articulated upwardly and downwardly.

In a non-limiting exemplary embodiment, the top portion 12 includes a plurality of holes 37. The plurality of fasteners 21 further include a tether 38 passed through the holes 37 and configured to secure to a head of the user so that the top portion 12 remains directly abutted against the nose bridge of the user while the bottom portion 16 remains abutted directly against the nostrils of the user. Such a structural configuration yields the new, useful, and unpredicted result of ensuring the scented air filter 20 is aligned with the user nostrils, and allows the mask 10 to remain engaged with the user face while the bottom portion 16 is articulated upwardly and downwardly.

Referring to FIGS. 1-6 in general, in a non-limiting exemplary embodiment, the nasal mask 10 may occasionally be used by children over the age of 12, but only with close supervision of a responsible adult. The nasal mask 10 has natural fruit oils or smells so that the user will experience the pleasant natural smell of fruit oils, floral extracts, or other means by which the device 10 is scented. The nasal mask 10 has unique features (e.g., open nostril area on the lower part of the apparatus; organic cotton mesh infused (impregnated) with scented oils; an inter-locking nodule located on the top portion 12 of the apparatus, to receive a hinge 15 and be able to temporarily not use the device 10, while still wearing the nasal mask 10. It can be used as a novelty item to promote sales for other products and/or maintain its own marketability through public exposure. For example, the nasal mask 10 structural configuration promotes use by those persons who would not otherwise submit to the changing a diaper.

In a non-limiting exemplary embodiment, the nasal mask 10 preferably has a nose-shaped or nose-covering construction made of either injected plastic molding from a rubber compound, or from a wax compound, which would contain the scented oils within the body 11 thereof.

In a non-limiting exemplary embodiment, the nasal mask 10 may have an open-bottomed structure having an aperture in each nostril portion for providing a dedicated air passageway under each user nostril and allowing filtered air flow into the user's nose. The bottom section is configured to fit snugly over and around the user's nose to only allow airflow to enter from the bottom portion 16 of the user's nose. Both sides of the top section rest on the user's nose, there are open holes 37 or slits for receiving an elastic band or tether 38 to wrap around the user's head, thereby maintaining the nasal mask 10 at a substantially stable position during use.

In a non-limiting exemplary embodiment, the nasal mask 10 has a single opening at the base of the nose, instead of a dedicated opening for each nostril. This single opening is triangular 44 so that the base of the nose is completely open and exposed to the scented material. A groove is cut or molded at approximately 0.5-1.0 cm from the bottom section of the nasal mask 10 to receive and secure the scented material slide. The bottom portion 16 is attached to the top portion 12 via a hinge 15 so that the bottom portion 16 can be selectively lifted away from the user's nostrils.

In a non-limiting exemplary embodiment, the nasal mask 10 includes a wax material that has been impregnated with the scent. The scent will last until the natural oils will no longer provide sufficient odor-masking support.

In a non-limiting exemplary embodiment, two separate arms are attached to the body 11 of the nasal mask 10 and wrap around a user's ears (similar to the arms on a pair of eye glasses) to support the nasal mask 10.

In a non-limiting exemplary embodiment, the nasal mask 10 may be maintained at an operating position by firmly deformably morphing the top portion 12 to match a contour of a user's nose and face. Adhesive fasteners 21 may be employed on the side of the top portion 12 which comes in direct contact with the user's skin. Pressure is applied to the top portion 12 for frictionally fitting and adhering the nasal mask 10 to the user face. For example, a thin piece of pliable, non-resilient, or bendable metal fastener may be positioned over a bridge of the top portion 12 and pinched along the user's nose bridge. The metal fastener maintains its morphed shape and keeps pressure along the bridge of the user's nose.

In a non-limiting exemplary embodiment, the elastic strap is either sewn together or its ends are removably attached to the sides of the top portion 12 thereby providing a looped fasteners 21 around the user's head. The width of the elastic strap may be 1/8 of an inch.

In a non-limiting exemplary embodiment, the plastic eye glass arms are attached to the slits located on either side of the top portion 12.

In a non-limiting exemplary embodiment, the nasal mask 10 may be supported by a string (tether 38) attached to each side of the top portion 12 so that it may be worn as a necklace. This way the nasal mask 10 is easily accessible to the user and can be applied and removed at will by the user.

In a non-limiting exemplary embodiment, a scented air filter 20 is removably inserted into the bottom portion 16 of the nasal mask 10. The scented air filter 20 includes organic cotton mesh so that air may freely pass through it in both directions when the user inhales and exhales. The scented air filter 20 may include fabric similar to tulle, only thicker and stiffer to provide adequate support during heavy breathing through the nose. The scented air filter 20 may include natural, recycled, processed, or compressed plant components such as hemp or another durable natural components. Various plants may be employed from which a fabric can be derived. The scented air filter 20 is impregnated with a fruit oil scent (primarily of citrus nature, particularly orange, which would specifically be named "Orange-U-Glad"). Lime, lemon and other natural flavors or oils can be used as well. The scented air filter 20 includes cotton or other fabric that slides into the bottom portion 16. The scented air filter 20 may be impregnated with a combined variety of natural fruit oils or other all natural floral oils or extracts. The scented air filter 20 is cut to shape to fit into the receiving slots of the bottom portion 16. The scented air filter 20 is removable/replaceable and can come in a variety of scents. The smell for the apparatus may be applied by soaking the scented air filter 20 in oils or extracts and left to dry.

In a non-limiting exemplary embodiment, the scented air filter 20 may be impregnated by an end user or pre-scented during a manufacturing process. The scented air filter 20 may also receive its scent by a variety of well-known processes that are economical and effective and safe. The scented air filter 20 preferably includes natural smells to last and provide pleasant aromas on the cloth. Another description of how to apply the scent to the cloth or fibrous material, is to have a small spray bottle that contains the natural fruit oils and or floral extracts. Fresh oils or scents or smells may be periodically sprayed on the cloth or fibrous material as needed. Such a cloth or fibrous material may be removably from the bottom portion 16 and may be reusable is needed, or may be designed for temporary use then discarded. Of course, additional pieces of cloth or fibrous material may be interchangeably inserted into the bottom portion 16.

While various embodiments have been described, the description is intended to be exemplary, rather than limiting, and it is understood that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claims require more features than are expressly recited in each claim. Rather, as the following claims reflect, inventive subject matter lies in less than all features of a single disclosed example. Thus, the following claims are hereby incorporated into the Detailed Description, with each claim standing on its own as a separately claimed subject matter.

What is claimed as new and what is desired to secure by Letters Patent of the United States is:

1. A nostril-shielding nasal mask for filtering ambient air prior to entering nostrils of the user, said nostril-shielding nasal mask comprising: an adjustable body configured to cover a nose bridge and nostrils of a user, said adjustable body including
   a top portion having a concave shape and being provided with an arcuate anterior face and arcuate posterior face opposed therefrom;
   a hinge attached to said top portion;
   a bottom portion attached to said hinge, said bottom portion having a planar shape and being provided with a curvilinear anterior face and a rectilinear posterior face, said bottom portion further having a plurality of apertures configured to align with the nostrils of the user, respectively;
   a scented air filter inserted through said rectilinear posterior face and into said bottom portion, said scented air filter being spaced from said top portion; and
   a plurality of fasteners attached to said top portion and said bottom portion, said fasteners being configured to maintain said top portion and said bottom portion directly abutted against the nose bridge of the user and the nostrils of the user, respectively;
   wherein said arcuate anterior face and said arcuate posterior face are solid and continuously extend between a top edge and a bottom edge of said top portion;
   wherein said plurality of fasteners include:
      a first finger statically attached to said arcuate anterior face and protruding outwardly away therefrom, and
      a notch disposed at said bottom portion and being configured to receive said first finger when said top portion is articulated to said first lowered, non-operating position;
   wherein said first finger is frictionally and detachably engaged with said scented air filter when said first finger is interlocked in said notch, said first finger being configured to maintain said scented air filter at said bottom portion when said top portion is articulated downwardly to said first lowered, non-operating position and while said bottom portion is articulated upwardly to said second raised, non-operating position.

2. The nostril-shielding nasal mask of claim 1, wherein each of said top portion and said bottom portion is configured to selectively articulated along a common arcuate path defined about a fulcrum axis of said hinge.

3. The nostril-shielding nasal mask of claim 2, wherein said bottom portion is configured to remain statically abutted directly against the nostrils of the user while said top portion is articulated along said common arcuate path between a first raised, operating position and a first lowered, non-operating position.

4. The nostril-shielding nasal mask of claim 3, wherein said top portion is configured to remain statically abutted directly against the nose bridge of the user while said bottom portion is articulated along said common arcuate path between a second raised, non-operating position and a second lowered, operating position.

5. The nostril-shielding nasal mask of claim 1, wherein said plurality of fasteners further comprise:
   a second finger and a third finger spaced therefrom, each of said second finger and said third finger being affixed to said top portion;
   a second notch and a third notch disposed at said curvilinear anterior face of said bottom portion;

wherein said second finger and said third finger are directly interlocked with said second notch and said third notch, respectively, when said top portion is disposed at said first raised, operating position and said bottom portion is disposed at said second lowered, operating position.

6. The nostril-shielding nasal mask of claim 5, wherein said apertures are equidistantly offset from a centrally registered latitudinal axis and configured to align beneath a respective one of the nostrils of the user, respectively.

7. The nostril-shielding nasal mask of claim 6, wherein said top portion includes a plurality of holes, and said plurality of fasteners further comprise: a tether passed through said holes and configured to secure to a head of the user so that said top portion remains directly abutted against the nose bridge of the user while said bottom portion remains abutted directly against the nostrils of the user.

8. A nostril-shielding nasal mask for filtering ambient air prior to entering nostrils of the user, said nostril-shielding nasal mask comprising: an adjustable body configured to cover a nose bridge and nostrils of a user, said adjustable body including
- a top portion having a concave shape and being provided with an arcuate anterior face and arcuate posterior face opposed therefrom;
- a hinge attached to said top portion;
- a bottom portion attached to said hinge, said bottom portion having a planar shape and being provided with a curvilinear anterior face and a rectilinear posterior face, said bottom portion further having a plurality of apertures configured to align with the nostrils of the user, respectively;
- a scented air filter removably inserted through said rectilinear posterior face and into said bottom portion, said scented air filter being spaced from said top portion; and
- a plurality of fasteners fixedly attached to said top portion and said bottom portion, said fasteners being configured to maintain said top portion and said bottom portion directly abutted against the nose bridge of the user and the nostrils of the user, respectively;
- wherein said bottom portion is indirectly attached to said top portion;
- wherein said arcuate anterior face and said arcuate posterior face are solid and continuously extend between a top edge and a bottom edge of said top portion;
- wherein said plurality of fasteners include:
  - a first finger statically attached to said arcuate anterior face and protruding outwardly away therefrom, and
  - a notch disposed at said bottom portion and being configured to receive said first finger when said top portion is articulated to said first lowered, non-operating position;

wherein said first finger is frictionally and detachably engaged with said scented air filter when said first finger is interlocked in said notch, said first finger being configured to maintain said scented air filter at said bottom portion when said top portion is articulated downwardly to said first lowered, non-operating position and while said bottom portion is articulated upwardly to said second raised, non-operating position.

9. The nostril-shielding nasal mask of claim 8, wherein each of said top portion and said bottom portion is configured to selectively articulated along a common arcuate path defined about a fulcrum axis of said hinge.

10. The nostril-shielding nasal mask of claim 9, wherein said bottom portion is configured to remain statically abutted directly against the nostrils of the user while said top portion is articulated along said common arcuate path between a first raised, operating position and a first lowered, non-operating position.

11. The nostril-shielding nasal mask of claim 10, wherein said top portion is configured to remain statically abutted directly against the nose bridge of the user while said bottom portion is articulated along said common arcuate path between a second raised, non-operating position and a second lowered, operating position.

12. The nostril-shielding nasal mask of claim 8, wherein said plurality of fasteners further comprise:
- a second finger and a third finger spaced therefrom, each of said second finger and said third finger being affixed to said top portion;
- a second notch and a third notch disposed at said curvilinear anterior face of said bottom portion;
- wherein said second finger and said third finger are directly interlocked with said second notch and said third notch, respectively, when said top portion is disposed at said first raised, operating position and said bottom portion is disposed at said second lowered, operating position.

13. The nostril-shielding nasal mask of claim 12, wherein said apertures are equidistantly offset from a centrally registered latitudinal axis and configured to align beneath a respective one of the nostrils of the user, respectively.

14. The nostril-shielding nasal mask of claim 13, wherein said top portion includes a plurality of holes, and said plurality of fasteners further comprise: a tether passed through said holes and configured to secure to a head of the user so that said top portion remains directly abutted against the nose bridge of the user while said bottom portion remains abutted directly against the nostrils of the user.

\* \* \* \* \*